US006821123B2

(12) United States Patent
Andersson et al.

(10) Patent No.: US 6,821,123 B2
(45) Date of Patent: Nov. 23, 2004

(54) ARRANGEMENT AND SYSTEM FOR PRODUCTION OF DENTAL PRODUCTS AND TRANSMISSION OF INFORMATION

(75) Inventors: Matts Andersson, Lerum (SE); Anders Törnquist, Gothenburg (SE)

(73) Assignee: Nobel Biocare AB, Göteborg (SE)

( * ) Notice: Subject to any disclaimer, the term of this patent is extended or adjusted under 35 U.S.C. 154(b) by 174 days.

(21) Appl. No.: 09/950,698

(22) Filed: Sep. 13, 2001

(65) Prior Publication Data

US 2002/0018981 A1 Feb. 14, 2002

Related U.S. Application Data

(63) Continuation of application No. 09/381,357, filed as application No. PCT/SE98/00493 on Nov. 2, 1999, now abandoned.

(30) Foreign Application Priority Data

Apr. 10, 1997 (SE) .............................................. 9701309

(51) Int. Cl.[7] .............................................. A61C 13/00
(52) U.S. Cl. ...................................... 433/215; 433/223
(58) Field of Search .............................. 433/215, 223, 433/213, 214

(56) References Cited

U.S. PATENT DOCUMENTS

| | | | |
|---|---|---|---|
| 5,368,478 A | * | 11/1994 | Andreiko et al. ............. 433/24 |
| 5,440,498 A | | 8/1995 | Timm |
| 5,453,009 A | | 9/1995 | Feldman |
| 5,497,338 A | | 3/1996 | Miyake et al. |
| 5,579,393 A | * | 11/1996 | Conner et al. |
| 5,652,709 A | | 7/1997 | Andersson et al. |
| 5,740,800 A | * | 4/1998 | Hendrickson et al. |
| 5,772,585 A | * | 6/1998 | Lavin et al. ................. 600/300 |
| 5,930,759 A | * | 7/1999 | Moore et al. |
| 6,032,119 A | * | 2/2000 | Brown et al. |
| 6,199,115 B1 | * | 3/2001 | DiRienzo |
| 6,212,442 B1 | | 4/2001 | Andersson et al. |

FOREIGN PATENT DOCUMENTS

| WO | WO 95/15731 | * | 6/1995 |
|---|---|---|---|
| WO | WO-96/37163 A1 | | 11/1996 |

* cited by examiner

Primary Examiner—Ralph A. Lewis
(74) Attorney, Agent, or Firm—Connoly Bove Lodge & Hutz LLP; Larry J. Hume (57) ABSTRACT

An operating site is used to assemble individually designed dental products, for example spacers, abutments, bridges, etc. Each product consists of two or more structural elements. The operating site is provided with computer equipment which can reproduce a simulated model of the jaw, jawbone, implant, etc., and structural elements applied to the model. The operating site is arranged to collate data in a profile relating to part of the assembly. Members are included for transmitting profile data via the network to the central unit. The central unit supplies information relating to the part in question. The information is sent to the operating site or to a production unit connected to the central unit for production of the part. A debiting system is arranged to indicate to the central unit or to the production site that the information or production, respectively, has been paid for.

21 Claims, 3 Drawing Sheets

ARRANGEMENT AND SYSTEM FOR PRODUCTION OF DENTAL PRODUCTS AND TRANSMISSION OF INFORMATION

CROSS-REFERENCE TO RELATED APPLICATIONS

This application is a continuation of U.S. patent application Ser. No. 09/381,357 filed on Nov. 2, 1999, now abandoned, which was a National Stage entry under 35 U.S.C. §371 of International Application PCT/SE98/00493, filed on Mar. 19, 1998, and which claims priority to Swedish patent application 9701309-8, filed on Apr. 10, 1997, the entire contents of each being incorporated by reference.

TECHNICAL FIELD

The present invention relates to an arrangement which makes it possible, at an operating site, to assemble individually designed dental products, for example distancing pieces, bridges, etc. Each dental product can in this case be made up from two or more structural elements. Each operating site is arranged with computer equipment with which it is possible to reproduce a simulated model of the jaw, dentine, implant, etc., and structural elements applied to the model. By means of interaction with the user, it is possible to adapt the constructional design of the respective assembled product to the dental situation in question. The operating site can be connected to one or more central units via a telecommunications and/or computer network, via which the central unit receives data from the operating site.

The arrangement can also be set up to permit manufacture of dental products, or instruments for the. latter, at a number of geographically distinct manufacturing sites, where the manufacturing procedure can be effected in a number of manufacturing stages.

The arrangement can also be set up so that, at one or more manufacturing sites, it is possible to control a manufacturing procedure for a dental product, or instrument for the latter, where the procedure comprises one or more subsidiary stages.

The arrangement can also be set up to assemble qualified constellations at a dental user site, for example with regard to dental situations, dental information, dental test products, etc. The user site has access to its own results or one or more presentation banks which can be subject to factual information relating to, for example, verifications, adjustments, complementary additions, etc. The user site can in this case be connected to one or more central units via a telecommunications and/or computer network, via which the user site and the central unit 5 are capable of exchanging information/data.

The invention is also applicable to a system for supplying dental products and preferably dental information relating to the products and dental situations and, if appropriate, also for making instruments for production of the product. A number of users using the system and constituting user sites can be connected to one or more central units, included in the system, via a telecommunications and/or computer network. The respective user site can in this case be provided with computer equipment by means of which query profiles can be collated.

STATE OF THE ART

It is already known to use mechanical, computer-aided methods for production of dental products such as caps, bridges, etc. Plaster models and the jaw, tooth remains, etc. of the patient can be scanned with the aid of various methods by the dental technician/dentist. The scanned information can be compressed and fed to the computer equipment, in which the model or equivalent can be simulated and, in the computer environment, can undergo constructional and add-on functions in order to obtain an optimum tooth replacement or equivalent for the patient in question. The result obtained can constitute the basis for ordering the actual dental product from a centralized manufacturing site. An order can be sent in a known manner to the manufacturing site or production site in question, which manufactures the desired dental product and sends this back to the orderer, who can then continue his work preparing and fitting the dental product on the patient.

In this connection, it is known to prepare not only tooth caps in this way, but also pontics, titanium crowns and bridge parts.

The users or the customers on the system thus provide for the system a work station which includes a standard PC with modem (or ISDN connection). The work station can be fitted out in various ways. Thus, for example, it can be equipped with a scanner device of the Procera type with associated user program.

DESCRIPTION OF THE INVENTION
TECHNICAL PROBLEM

The manufacturing process entails, overall, a very complex technique which it is not possible for each user/customer to perform. There is, however, a need for each user or customer to be able, to a greater extent than has hitherto been possible, to be able to gain access in a technically simple manner to all or parts of the complete process structure or process technique in order to obtain support, at the user site or customer site, for his own constructional and testing work on the respective patient. It is essential in this respect that use of the system is possible in a technically simple manner which has been well proven in the sector. The main object of the invention is to solve these problems.

There is also a need for the user to be able to subscribe to certain functions (structures) in the dental complex manufacturing process, which is being constantly updated and refined. Thus, for example, constant developments are being made on the software side, with the systems user (dentistldental technician) wishing to make use of these developments in their daily application, without too much work on updating requirements. The dentist/dental technician may require new reading and data compression systems and new hardware for these. By means of the invention, it is possible, in a simple manner, to have updating provided and installed in the customer equipment in a more or less automatic way.

Different users may be specialists in different dental products and dental situations, cf. titanium and ceramic crowns and bridges, and they may wish to consult the complex system only within their specialist area. The invention solves this problem too.

Users who need to use the complex system only now and then can also obtain help in a simple manner in the form of basic information. Thus, for example, it may be useful for a user/customer to find out about existing and well-proven constructions in specific dental situations. His/her work is made easier with a main-type solution to the specific dental situation. This is achieved, inter alia, by means of the fact that the system can give statistics and examples of use in different situations on which the user/customer/patient can base his solution.

Colleges and other educational institutions can also use the system as an information source for different dental situations and dental presentations.

It is also expedient, when using distancing pieces on or for implants, for these to be designed individually. The individual preparation can be based on information from the system, and the ordering and manufacture of the individually designed distancing pieces can be done with the aid of the system.

For the system provider, it is important to have a secure and reliable debiting system which executes debits for function uses and function means from the system and dental products or parts thereof manufactured in the system and instruments for the said products or parts. The invention solves this problem too.

There is a need to be able to expand the available equipment at the respective user site or customer site, and it is therefore desirable, for example, to be able to introduce and use a free-standing CADD program. As new software and hardware is developed, this too will be able to be connected to the work station, which in this way will be able to use the system to an even greater extent. There is therefore a need to be able to create a general IT-based dental platform (IT= information technology). In this way the customer can work with a Procerar station and send his work to a production unit via a network. The production unit then manufactures the component concerned and sends this to the customer. It will be possible to deal with all the administration in the given network. The invention solves this problem too.

The system will be able to be set up for a large number of work stations (customers). Thus, for example, the system will be able to be set up for several hundred work stations which will be able to be connected in stages without disrupting the rate of production of dental products and the delivery of information. Software used in the system will be able to be updated with minimal disruption to the production of dental products and delivery of information. This places special requirements on the coordination within the system. It additionally places requirements on the program constructions and how the programs are installed in the system. The invention is intended to solve these problems too.

There is therefore a requirement to be able to use routines for product modifications, which modification routines will be able to be used both for software and hardware. It is therefore expedient to be able to create a platform for comprehensive dental rehabilitation systems while at the same time being able to maintain the rate of development within the system. It is expedient in this case to be able to create a number of rules which mean that the routines in connection with the system are actually used. The invention also solves this set of problems.

SOLUTION

The feature which can principally be regarded as characterizing an arrangement used at an operating site to assemble individually designed dental products is that the operating site is arranged to collate data in a query profile relating to part of the assembly. The operating site is provided with members for transmitting query profile data via the network to the central unit. The latter is arranged, as a function of the received query profile data, to supply information relating to the part in question. This information can be sent to the operating site and/or can be set onwards to a production unit connected to the central unit, or included in the central unit, for production of the part. A further feature is that a debiting system is arranged to indicate to the central unit or to the production site that the information or production, respectively, has been paid for.

The query profile data can relate to queries on first information concerning the dental situation, which can relate to optimum design and fitting of the part concerned in the dental product in question. In one illustrative embodiment, the dental product can consist of a distancing arrangement on an implant. The distancing arrangement comprises an angled distancing part or other part which has on or more individual parameters, e.g. shape, position of rotation about the longitudinal axis of the implant, etc. The angled distancing part or the said other part is dependent on the individuality of the dental situation. In a further embodiment, the query profile data and the first information afford the possibility of interaction between the operating site's computer equipment, its user, and the central. unit for production of one or more structures adapted to the respective dental situation. In a preferred embodiment, a number of operating sites or customer sites are connected to the central unit and its production unit or production units. The operating sites are in this case categorized and each category subscribes to a relevant service which effects first information andlor product parts from the total range or offered range of the central unit and/or the production unit or production units. The first information can in this case relate to one or more computer program information items or computer programs for carrying out the said assembly. The query profile data of the respective operating site and the information sent from the central unit/respective production unit can preferably relate to user data and setting data for the scanner unit, measuring table, etc.

An arrangement used at a dental user site to assemble qualified constellations can principally be regarded as being characterized by the fact that the user site/customer site is arranged to collate data in a query profile relating to all or part of the constellation. The user site is in this case provided with members for transmitting query profile data via the network to the central unit. The central unit is arranged, as a function of the query profile data received, to supply factual information relating to the constellation or the constellations, which information can be sent back to the user site for acting on the said results or presentation bank/presentation banks. A further characteristic is that a debiting system is arranged to indicate to the central unit that the factual information sent out has been paid for.

In one embodiment, the factual information sent out consists of second information on manufacturing process (es) and/or statistics relating, for example, to the construction of different main types of dental products. In one embodiment, the central unit can also function is, or be connected to, one or more production units for production of dental products. The central unit and/or the respective production unit is arranged to utilize and store characteristic data on the dental products, data on the respective dental situation in which the respective dental product is being used, etc.

In a preferred embodiment, characteristic data thus utilized and stored and dental situations can be interrogated by means of the said query profiles from one or more user sites connected to the central unit 5 and/or the respective production unit.

The respective query profile data and returned information concern characteristics or construction information on different types of dental crown configurations which have been the object of production in association with manufacture/production controlled or managed by the central unit. The said types form main types which can each be supplemented by one or more variants.

An arrangement to permit manufacture of dental products, or instruments for the latter, at a number of geographically distinct manufacturing sites where the manufacturing procedure is effected in a number of manufacturing stages, is principally characterized in that a central unit supplies moduled information items and means for carrying out the stages, in which the different modules can be assigned to the different manufacturing stages or parts thereof. The different manufacturing stages are capable of interrogating and/or are assigned in advance one or more of the said moduled information items and means in order to be able to carry out all or part of the manufacturing process by means of the called-up information items and means. Transmission members are arranged, as a function of the requested order for called-up information and means, to effect transmission of these on a computer and/or communications medium which connects the respective manufacturing site to the central unit. In this case too, a debiting system is arranged to credit the central unit with payment for used time, information and/or means.

In a preferred embodiment, the customers are categorized in such a way that a first category of customer can be assigned first information and means, a second category of customer can be assigned second information and means, etc. The said information and means can comprise control information for operating equipment for one or more of thesaid manufacturing stages at the manufacturing site.

An arrangement used at one or more manufacturing sites to control a manufacturing procedure for a dental product, or instrument for this, where the manufacturing procedure comprises one or more subsidiary stages, can principally be regarded as being characterized by the fact that the control information for equipment effecting one or more manufacturing procedures or subsidiary stages thereof can be extracted by a selection procedure from an information and/or data bank located in a unit geographically separated from the respective manufacturing site. Extraction is in this case carried out by means of the selection made at the respective manufacturing site, and the selection made can be transferred via a computer and/or telecommunications medium to effect selection in the information and/or data bank at the central unit. As a function of the selection, the central unit transmits the selected information and/or means. At the manufacturing site, the selected information received is arranged to be included in or be converted to control information for the equipment in question. Here, once again, use is made of debiting equipment which credits the central unit with payment for used time, information and/or means.

A system in accordance with the above can be regarded as being characterized by the fact that the said central unit(s) comprise(s) one or more coordinating units which, via afirst telecommunicationsand/or computer network or a second local telecommunications and/or computer network, is/are connected to one or more production units. The respective coordinating unit is in this case arranged to effect or participate in the assignment of the information flows coming from the user sites/customer sites via the first telecommunications and/or computer network (query profile data). The respective production unit functions as order receiver for the respective dental product which the respective user site wishes to have produced.

In a preferred embodiment, the respective user site is equipped with functions for readingoff the model or jaw, dentine,etc., of the patient. The reading result can be fed to the user site's computer equipment, and a query profile (systems user profile) effected by this means includes one or more tasks. The respective coordinating unit preferably functions as a connection station to a network (telecommunications and/or computer network) belonging to the system. Two or more coordinating units distribute the incoming query profile flow (systems user flow) and the flow of information coming from the coordinating units, which information, for example, will be controlled for access to different databases. The system capacity can be expanded by means of connection of further coordinating units and/or inclusion of more powerful computers in existing coordinating units and/or connection of several ISDN modems.

Further characteristics of the system will be evident from the subsequent system subclaims.

ADVANTAGES

The features proposed above provide a system and a user relationship characterized by economic application of the system from the viewpoint of the user sites /customers. Use is based on technology which is known per se, and which further affords simplified use procedures for the users, while maintaining economic advantages. The users, i.e. dentists/ dental technicians, can make use of the advantages obtained through high manufacturing operations, involving substantial economic and technical outlay. By means of the fact that subsidiary functions, statistics, etc., are offered for sale in the large system, the developments in this system can benefit the users against payment for only the desired use. Very considerable experience of manufactured products, product designs, etc., can be built into and stored in the system. The stored information can be used as basic information for the users and for statistical application in association with colleges and other institutions. In addition to offering accurate and exact products, the system provider can receive payment for continued development and research. The very substantial development of the databases in the coordinating units means that it is possible to follow everything that is going on in the system. Production can be constantly modified and administrative functions can be applied in the databases in order to facilitate the development work. Despite the information content being transferred in the proposed manner. to the user sites/customers, the required accuracy of the products can be maintained. The required accuracy nowadays is about 2/100ths tolerance.

DESCRIPTION OF THE FIGURES

A presently proposed embodiment of an arrangement and a system according to the invention will be described hereinbelow with reference to the attached drawings, in which.

DETAILED EMBODIMENT

Figure 1:
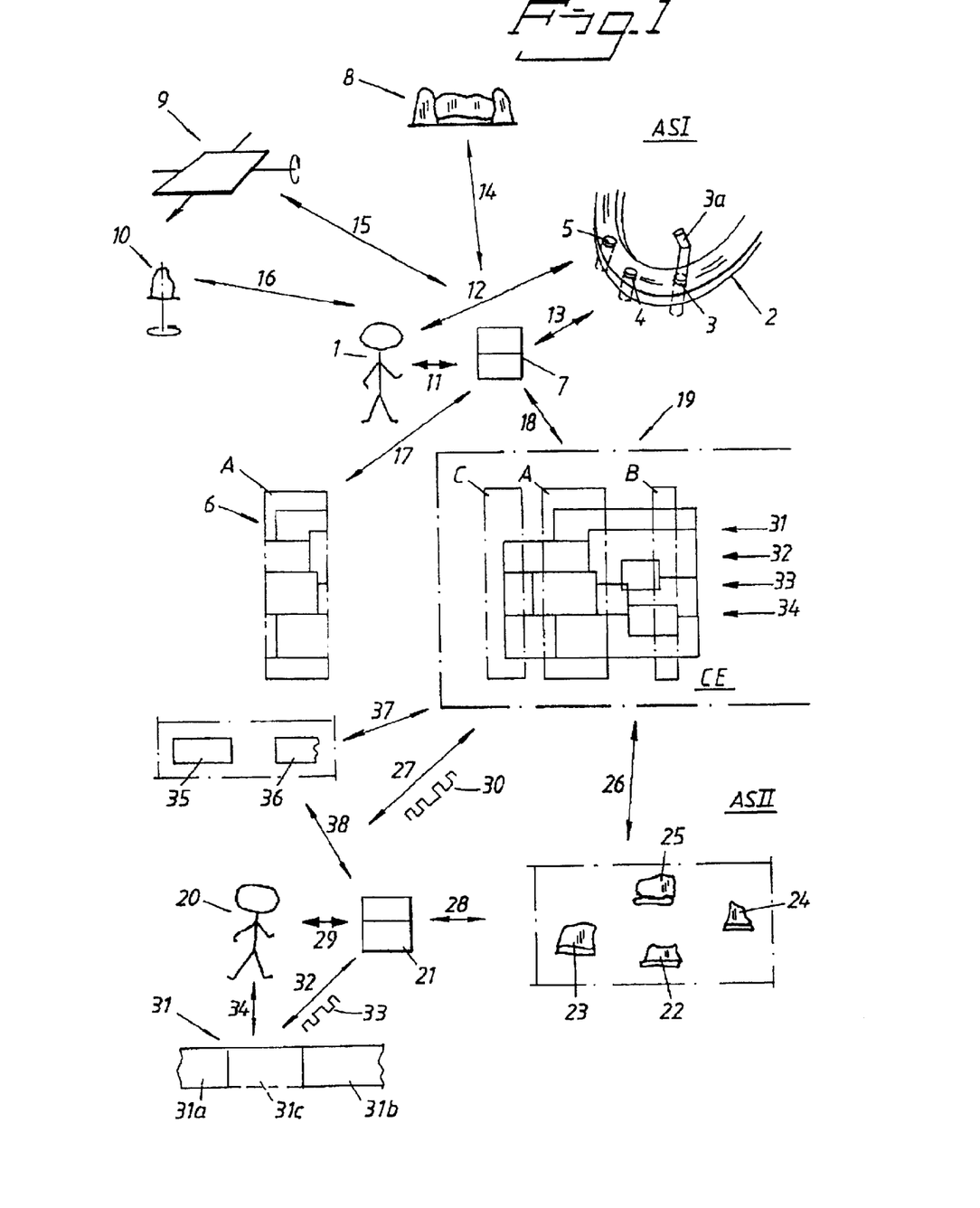
FIG. 1 is an outline diagram showing the connection of two user sites/customers to a central unit, where the two users or customers represent different categories for use of different functions in the complex system at the central unit.

In FIG. 1, a first user is indicated by 1. The user works, inter alia, with a model 2, in which implants 3, 4, 5 are arranged. In or on the implant 3 there is an angled distancing piece 3a which is individually designed for the patient/dental situation in question. The user 1 has a production resource 6. A user site for the user 1 is indicated by ASI. The user 1/user site ASI has access to computer equipment 7. The user 1 can also work with a dental product in the form of a dental bridge 8. In addition to the product resource 6 and other equipment, the user/user site can have access to levelling table 9 for production of the dental product, reading equipment 10, etc.

The manufacturing method for producing dental products in accordance with the above with the aid of the said equipment is already well known and will not be described here. However, the possibility of interaction between the user 1 and the computer equipment 7 is indicated symbolically by arrows 11. Interaction between user 1 and model 2 is indicated by arrows 12. The simulation and production of the model 2 in the computer equipment 7 is shown by arrows 13. The use and supply of information between the bridge part B, levelling table 9 and scanning equipment 10 and the user 1 and computer equipment 7 are symbolized by arrows 14, 15 and 16. Relations and interaction between the computer equipment and the production resource 6 are symbolized by 17. A manufacturing and information supply site is indicated by CE, and transmission via a telecommunications and/or computer system between the user site ASI and the site CE is indicated by arrows 18. The site CE can be regarded as central equipment in relation to the user site.

In accordance with the invention, the user 1/user site ASI subscribes to or purchases information or orders products from the system 19 in the central unit CE. The system 19 is technically complex and includes manufacturing processes for production of titanium crowns, ceramic crowns, caps, bridges, statistics, programs, etc. The various functions machinery, information, etc., can be categorized, and FIG. 1 shows the categories A, H and C. In the present case, the user 1 has purchased or subscribed to information relating to category A, which information is used by the user 1 to assist in his work and make it more efficient. This work can involve producing an angled distancing piece 3a, in which work his purchased or subscribed information, data, programs, etc., can be used to produce an actual dental assembly 3+3a with the computer equipment 7. In accordance with the invention, he can obtain help in producing a dental bridge 8. He can also obtain control information on his levelling table 9 and/or information on reading of an actual product. In accordance with the concept of the invention, it is also possible, as a function of his constructional and test work, to make a product with the aid of the information obtained from the system 19, and the computer equipment 7, and to order the latter in the central unit CE.

FIG. 1 also shows a second user site ASII with user 20. This user has, in corresponding manner, computer equipment 21. The user 20 may be interested in another type of information than that in the case of the user 1 described above. Examples of such information are statistics from different main types of dental crowns 22, 23, 24, 25. These statistics can be used as a basis for starting up dental fitting work in or on a patient. The statistics can also be used in different combinations and assessment situations. The acquisition of the statistics from the system 19 is symbolized by arrows 26. The user 20 uses his computer equipment 21 to send a query profile via a connection (telecommunications and/or computer connection) which is symbolized by arrows 27. The input of statistics for the dental crowns in the computer equipment is symbolized by arrows 28. The interaction between the computer equipment and the user 20 is symbolized by arrows 29. The actual query profile which is generated by the user 20 with the aid of the computer equipment 21 is sent to the central unit CE in digital form, and such a query profile is symbolized by 30. The query profile triggers selection information 31, 32, 33 and/or 34 in the central unit CE. By means of the selection information, the information on the dental crowns 22, 23, 24 and 25 can be transmitted via an actual connection 26 or 27. The user 20 can, with the aid of the information in or from the system 19 in the central unit CE, build up an actual constellation 31 which can consist of previously known parts 31a and 31b, which the user 20 needs to supplement with factual information 31c from the system. The factual information can be transmitted from the computer equipment 21 via a connection which is symbolized by arrows 32. Alternatively, the factual information can be stored up and used in the computer equipment 21. Factual information is also transmitted in digital form and is symbolized by 33. The constellation construction which is carried out by the user 20 is symbolized by arrows 34. The user can also request program 30 information 35, 36 from the system 19. Such program information, and its relation to the system, are symbolized by arrows 37. The transfer of the program to the computer equipment 21 is symbolized by arrows 38.

Figure 2:
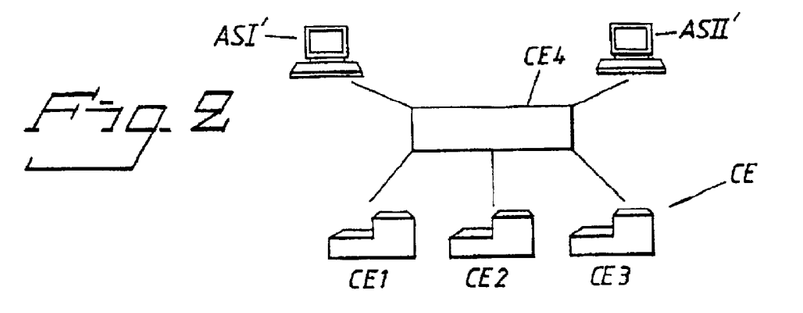
FIG. 2 is an outline diagram showing the connection of the user site/customers to production units via a network of the Procera type.

FIG. 2 shows that the central unit CE can comprise different units, for example production units CE1, CE2 and CE3, and a network CE4 with associated coordinating units, which are described hereinbelow.

Figure 3:
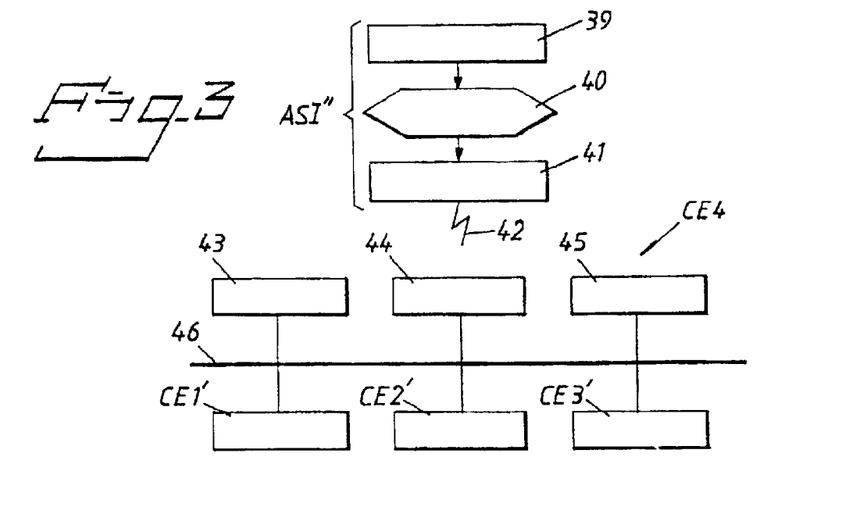
FIG. 3 shows, in a block diagram, the structure of a user site.

FIG. 3 shows an example of the construction of a user site/customer ASI". In accordance with the above, the user site can include a process scanner/reader 39 of known type, for example a Procera scanner station. The scanner station can produce a query profile which is symbolized by 40. The query profile is generated with the aid of a CADD program known per se, for example the Procera CADE program. The program handles filling-in and ordering functions in a manner known per se. The user site ASI" also includes a modem which can be of a type known per se. Thus, for example, a modem 40 of the ISDN type can be used. The modem connects the work station, or renders it connectable, to a connection symbolized by 42 in a computer network. The network part CE4 (cf. FIG. 2) comprises a number of coordinating units. FIG. 3 shows three coordinating units 43, 44, 45. The coordinating units form a common network with the production units CE1', CE2', CE3' (cf. FIG. 2). The network connection is symbolized by 46. The information flow, when ordering a dental cap for example, can be described by the following work stages. Reading off the plaster model, filling-in of dental data, patient, tooth, ED type, type of work, etc., processing of data file in Procera CAD, filling-in of order form and dispatching of the order. The order is implemented by the equipment being coupled up to one of the Procera coordinating units. Here, the order is received, confirmed and sent onwards to one of the production units. The different customers (cf. the users 1 and 20 in FIG. 1) can couple up to one of the said coordinating units and send their order on. The coordinating units provide the possibility of access to different databases, for example product registers or other product information, cf. below.

There is also the possibility of providing ongoing information on the present order and previous orders.

Figure 4:
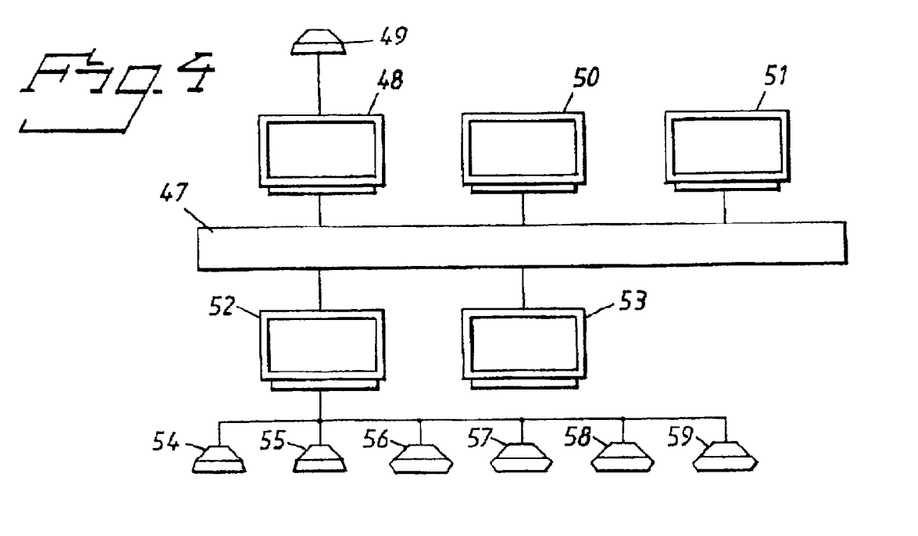
FIG. 4 shows, in a block diagram, the structure of a coordinating unit in the network according to FIG. 2.

FIG. 4 shows a coordinating unit which in principle functions as a connection station to the Procera network. The purpose of several coordinating units is, on the one hand, to be able to distribute the incoming information flow in the form of the said orders, and, on the other hand, to distribute the outgoing information flow, which can consist, for example, of access to different databases. As, the flow of information increases, with new customers and services being added, the system capacity can be increased either by connection of several coordinating units or by equipping the respective coordinating unit with more powerful computers and more modem/ISDN connections. The coordinating unit is constructed as a local network. If several coordinating units are coupled together, these can be made to act as a common network. The local network 47 is an LAN (Local Area Network). In FIG. 4, a transport server is shown by 48, and an ISDN connection arranged on the latter is shown by 49. Further servers are shown by 50, 51, 52 and 53. The server 52 is connected via ISDN connections 54 and 55 and modems 56, 57, 58 and 59. The server 53 is used as file server. The server 51 is coupled up as database motor. The server 52 constitutes an RLN server (Remote Lan Node). The latter server represents the respective client and forms the input and output channel of the coordinating unit.

Figure 5:
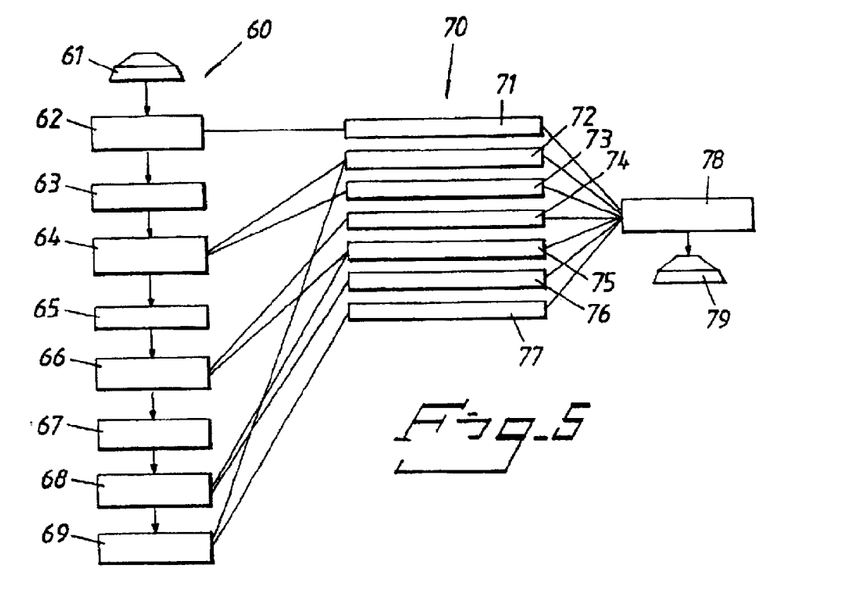
FIG. 5 shows the flow of information, of query profile data from the user site, being received in a coordinating unit.

FIG. 5 shows the data flow in a production 25 unit. Each event in the production unit is registered, in different databases. The information in the databases is sent onwards to the coordinating unit or the coordinating units. The incoming order flow is shown by 60. The incoming connection is 61. Incoming orders are registered in block 62. 63 symbolizes a library for registration of incoming orders. Orders are registered in 64, and 65 indicates a data library. File preparations are made in 66, and 67 indicates a preparation library. 68 treats data on the milling process, and 69 indicates the flow registration 70 symbolizes database applications, where a first application 71 indicates incoming data, a second application 72 indicates financial data, a third application 73 indicates datafiles, a fourth application 74 indicates file preparations, a fifth application indicates production administration data, a sixth application 76 indicates milling or machining data, and 77 constitutes address information. The coordination between the incoming flow 60 and the database applications is achieved in a manner known per se and is shown by different connections. The database applications are connected to the coordinating unit via a transport server 7B which is provided with an output connection 79.

Figure 6:
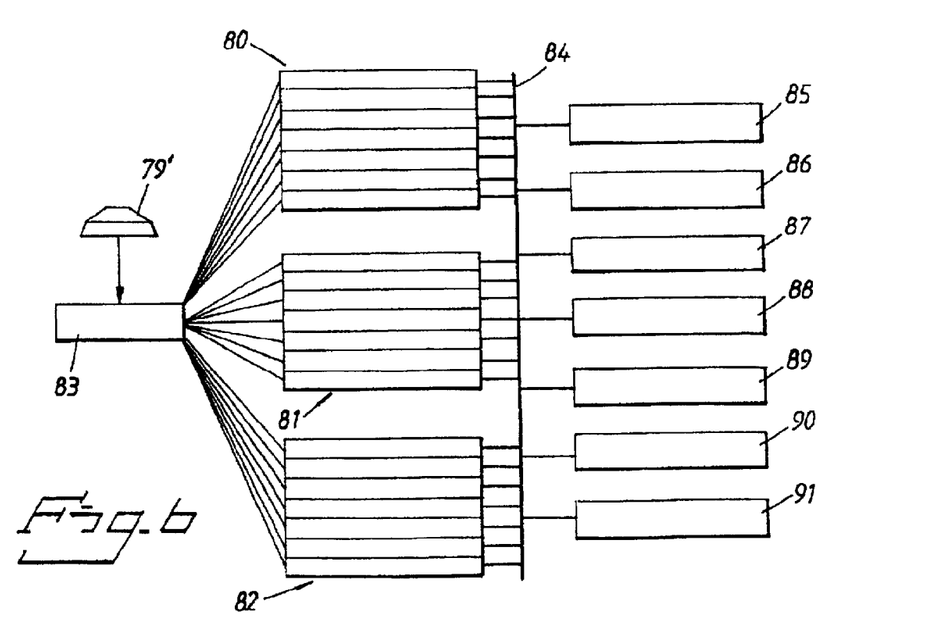
FIG. 6 shows databases in the production units and coordinating units connected to the databases and EQL database applications.

FIG. 6 shows the construction of three different product units 80, 81 and 82. The product units are designed in essentially the same manner. The different production units can constitute different types of dental products, for example titanium bridges, ceramic crowns, etc. Each production database 80, 81 and 82 has a construction corresponding to the database constellation 70 in FIG. 5. An input connection is indicated by 79' and a transport server by 83. At their outputs, the database parts 80, 81 and 82 are connected to a line system 84. Connected to the latter is a system for financial reporting 85, a system for specifications B6, a system for article indexing 87, a system for customer indexing 88, a system for client registration 89, a system for client database 90, and a system for production modifications 91.

Updating of the coordinating units is done by so-called data replication. Data replication is carried out so that one has several identical databases. These databases are updated by transferring only information which has been modified since the preceding update. By using this technique, it is possible to expand the system for several users and/or several applications without limit. The database applications 85–91 work using SQL (Structured Query Language). There are therefore copies of the databases from all the production units. The databases are constantly updated by means of data replication. The database applications can then take information from the production units databases. The system is expanded by creating more coordinating units. The said coordinating units then receive a complete set of databases.

The invention also relates to a method using one or more computers or computer units to generate a system protocol for the process of production of a dental product, for example all or parts of one or more dental crowns, one or more dental bridges, etc., or instruments for these. The system is generated on the basis of, inter alia, a construction of the product or instrument simulated at a customer site, which can be a dental practice, dental technician's workplace, etc., in a computer environment in a manner known per se. In this case, the computer environment has access to first data concerning a basic protocol relating to production of a basic variant of the dental product or instrument. A supplementary protocol is generated by means of second data generated as a function of the construction simulated at the customer site. In an interaction between the respective computer unit and user, the system protocol is generated on the basis of the said first and second information. The basic protocol can in this case be selected from among a number of existing basic protocols which represent different variants. The basic protocol variants can be produced as a function of statistics from previous treatments in accordance with the above. The system protocol can be produced at the central unit or at the respective customer site or at one or more of the customer sites. The respective customer site is debited by means of debiting equipment (cf. above) for use of the various data from the central unit.

The invention also relates to a method and arrangement using one or more computer units to generate a program for reproducing visually on the computer screen all or part of a product, for example all or part of one or more dental bridges, one or more dental crowns, etc., or instruments for these. The generation takes into account a construction simulated at a customer site, for example at a dental clinic, dental technician's workplace etc., in a computer environment. The said computer environment is supplied with first data attributable to a basic program for reproduction and presentation on the computer screen of a basic variant of the dental product/instrument. The said computer environment is also supplied with second data attributable to an add-on program which permits addition of characteristics to the basic variant by interaction between the computer unit/computer units in question and one or more users. The said first and second data can be transmitted from the central unit to a customer site, and the content or use time of the data in question can be priced with the aid of debiting equipment.

The methods and arrangements described above can also be characterized by the fact that the transmission between a central unit and a customer site is effected wholly or partly via the internet, i.e. the international telecommunications and/or computer network. The invention also relates to an arrangement for a system for producing dental products, in which a number of customer sites (dentists, dental technicians, etc.) are served by one or more central units which supply the respective customer site with dental products, instruments for production of dental products, information on dental products, instruments, statistics, and the like. The arrangement is in this case characterized by a queuing facility which is arranged to provide the respective customer site with details on the delivery time of the requested product/instrument or information. The operation can then be accomplished as a function of an order or request from the customer site in a manner known per se. The information in question can include concrete time indications of the delivery.

The invention is not limited to the embodiment described above, but can be modified within the scope of the attached patent claims and the inventive concept.

What is claimed is:

1. A system to assist in production of a dental assembly, such as a bridge or spacer, where the assembly is made from a plurality of elements, the system comprising:
   a plurality operating sites each including:
      a computer display to reproduce a representation of a jaw, jawbone or dental implant and structural elements to be applied thereto for user interaction to control product design,
      means to assemble data relating to only a portion of the dental assembly into a profile, and
      means to transmit the profile to a central site,
   the central site including:
      means responsive to receipt of the profile for identifying stored information and supplying the stored information to a recipient location,
      accounting means for recording billing data related to supply of the stored information, and
      a telecommunications network connecting the operating site and the central site,
   wherein a profile associate with each of the operating sites relates to a different portion of the dental assembly.

2. A system as recited in claim 1 which further includes a production subsystem connected to receive the stored information.

3. A system as recited in claim 2 wherein the production subsystem is located at the central site.

4. A system as recited in claim 2 wherein the production subsystem is located remote from the central site.

5. A system as recited in claim 1 wherein the recipient location is the operating site.

6. A system as recited in claim 1 wherein the profile describes a dental situation for application of the product.

7. A system as recited in claim 6 wherein the product is an angled spacer for an implant having one or more parameters selected for the dental situation of a particular patient.

8. A system as recited in claim 7 wherein the parameters are selected based on interaction between the profile and the stored data.

9. A system as recited in claim 1 wherein each of the plural operating sites subscribe to a particular service which is a subset of the services available from the central site.

10. A system as recited in claim 1 wherein the stored information relates to a program or program information item.

11. A system as recited in claim 1 wherein the stored data includes data for setting or controlling components at a user site.

12. A subsystem used at a dental user site to assemble reconstructions for particular dental situations applying dental information and products, the subsystem sending data to a central site and receiving related factual information therefrom, said subsystem comprising:
   means to assemble data into a profile relating to only a portion of the reconstruction,
   means to transmit the profile to the central site,
   means responsive to the factual information from the central site,
   presentation means responsive to the profile data and to the factual information, and
   accounting means for indicating to the central site payment for the factual information.

13. A subsystem as recited in claim 12 wherein the factual information relates manufacturing processes and/or statistics relating to dental products and/or situations.

14. A system including the subsystem of claim 12, a central site and one or more production units for the production of dental products and/or instruments, the central site including
   means for receiving profile data from a user site and for selecting, based on the received profile data, related factual data,
   means for transmitting the selected factual data to the user site, and
wherein the production unit includes:
   means to manufacture, analyze and store characteristic data on dental products wherein the characteristic data may be interrogated by the profile data.

15. A system as recited in claim 14 wherein the profile data and the returned factual infornmation involve construction information on different types of crown configurations where the types form main types which may be supplemented by one or more variants of the main types.

16. A manufacturing system for manufacturing a dental or dental related assembly including a subsystem employed at two or more manufacturing sites for the manufacture of the dental or dental related assembly, wherein the manufacturing procedure can be effected in stages at each or the two or more manufacturing sites by:
   (a) reading or scanning data related to only a portion of the assembly,
   (b) transforming and transmitting the data from stage (a),
   (c) representing the data from stage (b) in a computer environment,
   (d) input of adjustments or additions to the representation of stage (c),
   (e) physical production of portion of the assembly from or with a blank, and
   (f) testing the portion of the assembly, the system comprising:
      a central unit for supplying information corresponding to the two or more manufacturing sites,
      a telecommunications medium connecting the central site and the two or more manufacturing sites,
      transmission means for transmitting the information over the telecommunications medium, and
      accounting means for billing for the time or information resources employed.

17. A manufacturing system as recited in claim 16 wherein the information is categorized by category of customers.

18. A manufacturing system as recited in claim 16 wherein the information is control information for operating manufacturing equipment for one or more of the stages of manufacture.

19. A manufacturing system for manufacturing a dental or dental related product including subsystems employed at each of two or more manufacturing sites for the manufacture of the dental or dental related product, wherein the manufacturing procedure at each of the two or more manufacturing sites can be effected in stages including:

(a) reading or scanning data related to a portion of the product,
(b) transforming and transmitting the data from stage (a),
(c) representing the data from stage (b) in a computer environment,
(d) input of adjusts or additions to the representation of stage (c),
(e) physical production of a portion of the product from or with a blank, and
(f) testing the portion of the product,
the system comprising:
    means for extracting control information for equipment effecting one or more of the procedures of the manufacturing stages from a data bank remote from the equipment,
    means for initiating the extraction by a selection made at the site of the equipment.
    means for transferring, via a telecommunication medium, t selection to the data bank,
    means for transferring the selected control information to the equipment, and
    accounting means for billing for the time and information resources employed,
wherein each of the two or manufacturing sites produces a different portion of the product.

20. A system for supplying dental products and information, the system including:

plural user sites connected to one or more central units via a first computer network and where a user site is provided with computer equipment for assembling a profile representing only a portion of one or more of the dental products, a central unit comprising one or more coordinating units which, via the first computer network or a second computer network is connected to one or more production units, the coordinating units direct information from user sites via the first computer network, and the production units receive orders for respective different portions of the dental products from user sites.

21. A system as recited in claim 20 wherein a user site includes:
    means for scanning or measuring a model, jaw, or jawbone,
    means for applying the data from the scanning or measuring to the user site computer equipment, and where the computer equipment produces a profile allowing for further input of dental data patient identification, tooth identification, or type of work,
    means for processing the data further input, and
    means for transmitting and order containing some of the further input data over the first computer network.

\* \* \* \* \*